(12) United States Patent
Collins

(10) Patent No.: US 10,239,057 B2
(45) Date of Patent: *Mar. 26, 2019

(54) MICROFLUIDIC DEVICES AND METHODS FOR CELL ANALYSIS AND MOLECULAR DIAGNOSTICS

(71) Applicant: John Collins, Irvine, CA (US)

(72) Inventor: John Collins, Irvine, CA (US)

(73) Assignee: Biopico Systems Inc, Irvine, CA (US)

(*) Notice: Subject to any disclaimer, the term of this patent is extended or adjusted under 35 U.S.C. 154(b) by 353 days.

This patent is subject to a terminal disclaimer.

(21) Appl. No.: 14/733,539

(22) Filed: Jun. 8, 2015

(65) Prior Publication Data
US 2016/0207044 A1     Jul. 21, 2016

Related U.S. Application Data

(62) Division of application No. 13/464,893, filed on May 4, 2012, now Pat. No. 9,110,026.

(51) Int. Cl.
| | |
|---|---|
| *B01L 3/00* | (2006.01) |
| *B01L 7/00* | (2006.01) |
| *C12Q 1/68* | (2018.01) |
| *C40B 60/08* | (2006.01) |
| *G01N 21/64* | (2006.01) |
| *C12Q 1/24* | (2006.01) |
| *C12Q 1/686* | (2018.01) |

(52) U.S. Cl.
CPC ... *B01L 3/502761* (2013.01); *B01L 3/502715* (2013.01); *B01L 7/52* (2013.01); *C12Q 1/24* (2013.01); *C12Q 1/686* (2013.01); *G01N 21/6486* (2013.01); *B01L 2200/0668* (2013.01); *B01L 2200/0673* (2013.01); *B01L 2300/0816* (2013.01); *B01L 2300/0819* (2013.01); *B01L 2300/185* (2013.01); *B01L 2300/1822* (2013.01); *B01L 2300/1894* (2013.01); *B01L 2400/0415* (2013.01); *B01L 2400/0427* (2013.01); *B01L 2400/0445* (2013.01); *B01L 2400/0487* (2013.01); *B01L 2400/086* (2013.01); *C40B 60/08* (2013.01)

(58) Field of Classification Search
None
See application file for complete search history.

(56) References Cited

PUBLICATIONS

Huebner et al., "Static microdroplet arrays: a microfluidic device for droplet trapping, incubation and release for enzymatic and cell-based assays," Lab Chip 2009, 9:692-698.*

\* cited by examiner

*Primary Examiner* — Kaijiang Zhang

(57) ABSTRACT

Microfluidic devices and methods that use massively parallel anchored picoreactors as the basis for cell and molecular diagnostics are included in this invention. Different processes such as isolation, processing, amplification and characterization of different fluids, particles, chemical compositions or biospecies are presented. These fluids include biochemical buffers or cellular products including different cells, biochemical compositions, proteins and enzymes.

16 Claims, 14 Drawing Sheets

Figures 1A, 1B, 1C, 1D, 1E:
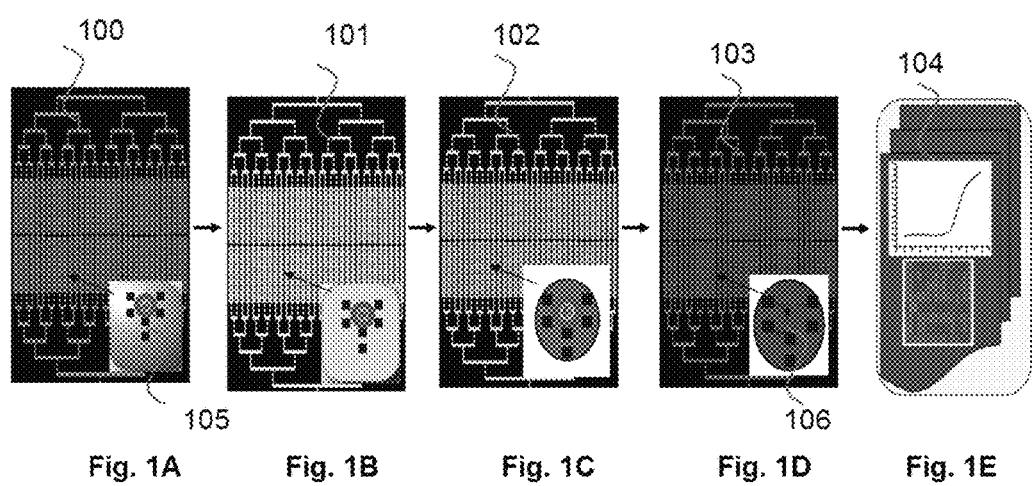

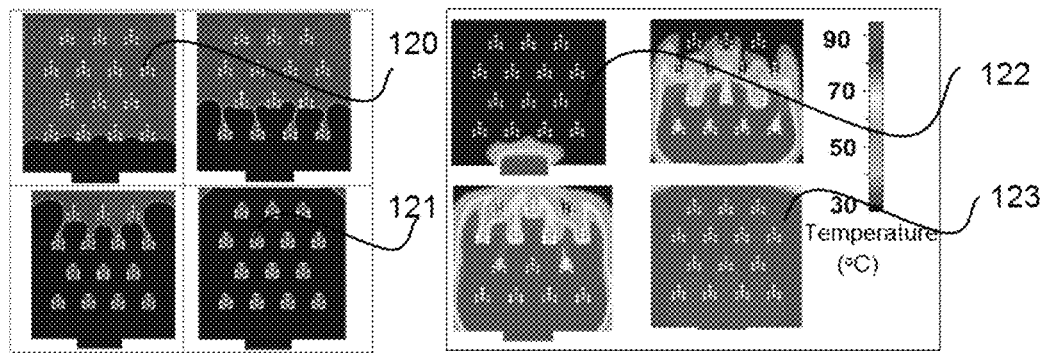
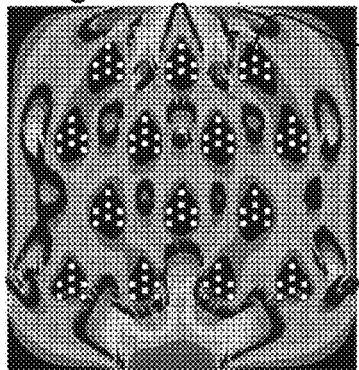
Fig. 2C
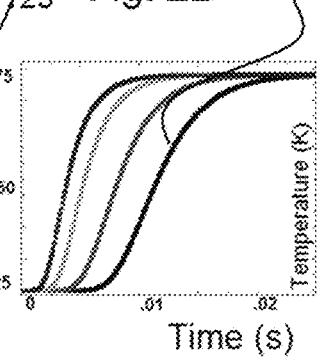
Fig. 2D
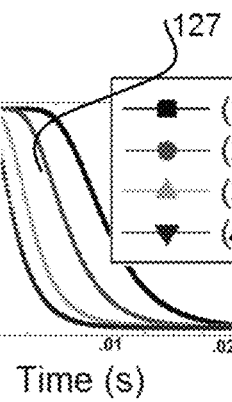
Fig. 2E
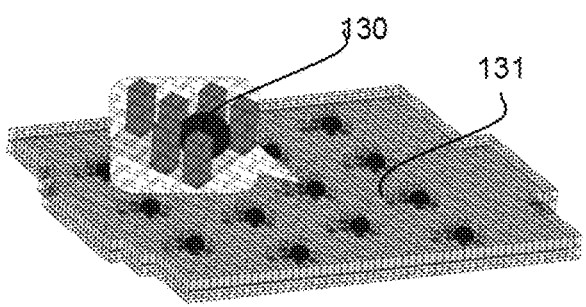
Fig. 2F
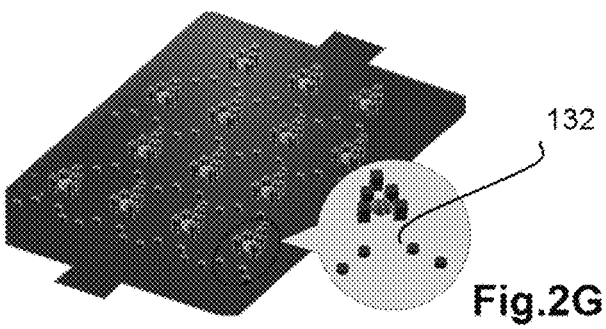
Fig. 2G 140
141
142

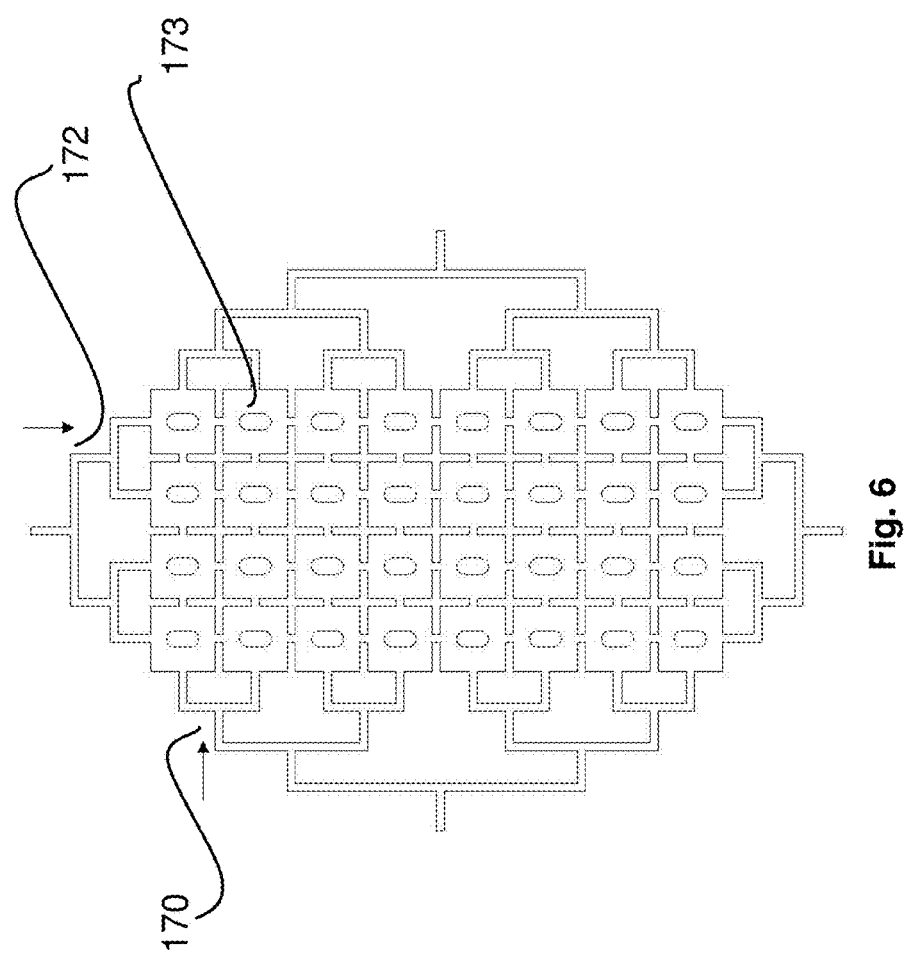

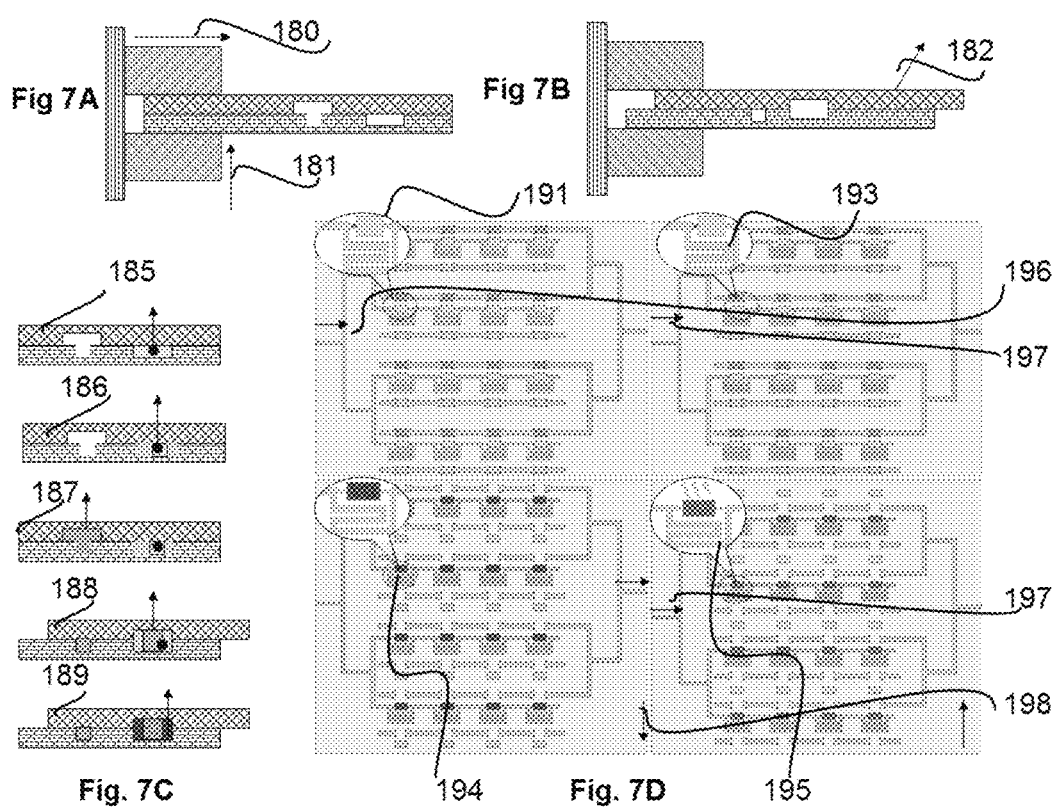

MICROFLUIDIC DEVICES AND METHODS FOR CELL ANALYSIS AND MOLECULAR DIAGNOSTICS

RELATED APPLICATION

This application claims priority to U.S. Provisional Patent Application No. 61/482,997 filled on May 5, 2011, the entirety of which is expressed incorporated herein by reference.

DESCRIPTION

Field of the Invention

The present invention relates generally to medical devices and methods and more particularly to microfluidic devices and methods that involve massively parallel picoreactors based processing of cells and molecules for single cell analysis, cell based assay or diagnostics.

Background of the Invention

Micrototal analysis systems of the prior art have typically involves microdroplets formation followed by cells and molecules encapsulation. These technologies require external active instruments to accomplish medical diagnostics which will be difficult to perform one touch or one step device operation. On the other hand, in our technology, single or multiple cells or molecules are trapped first either at configured micropillars or nozzles and then picoliter volume reservoirs or reactors are formed around the single or multiple cell using immiscible fluidics. The isolated single cell or cells or molecules are processed for multistep temperature reactions or chemical reaction. Multiple temperature biochemical reaction such as PCR or linear isothermal amplification can be carried out on the trapped picoreactors by flowing immiscible fluids such as oil, fluorocarbon fluids around the picoreactors. Further, if needed, a slip and lock chip technique supplies additional reagent from another layer of microfluidic chip. PCR using fluid flow thermal cycling is also highly innovative. The dimensions of the pillars for trapping cells and flow rate of the oil for encapsulating single cells are optimized for the efficiency and specificity of the diagnostics device.

Biochemical analysis of single cells is of significant interest to the biological, medical, and pharmaceutical communities. Such biochemical analysis on abnormal gene and proteins are very significant for early disease diagnosis. The primary problems that hinder such diagnosis are difficulty in handling a minute amount of sample, inability to prepare and manipulate a single cell, inability to have high-throughput capability, and not being integrated with amplification protocols and detection mechanisms. As it is extremely labor intensive and requires expensive equipment to isolate single cells and perform amplification on each cell, the cell number that can be tested each time is very limited and the procedure is very time consuming. Precise molecular analysis on single cells from a large population of cells led to the enumeration of cells with specific genes. Microfluidic technologies and automation of biochemical analysis helps in the process control needed to ensure reliability of such diagnosis. The application of this technology is in the diagnostics of various diseases such as different chromosomes aberrations in leukemia, HIV/AIDS, prenatal diagnostics, infectious diseases, saliva based detection. The current methods are limited by long turnaround times, high cost, labor intensiveness etc.

The system combines fluorescent RT-PCR, immiscible microfluidics, and single cell microtrapping technologies to carry out single-cell PCR in a quick, high-throughput, and cost-effective fashion for clinical diagnostics or biomedical research purposes. Thus, there exists a potential for development of devices and methods which utilize massively parallel picoreactors as the basis for the diagnostics and processing of molecules and cells (e.g., cell characterization, cell isolation, molecules amplification, sensing distinguishing different biochemicals).

Further, encapsulation of oil around cells for isolating reactor system can be used for drug screening application. Traditional parallel culture platforms are not suitable for screening and identifying combination therapy candidates as they do not facilitate the on-chip generation of pair-wise concentration ranges needed for such experiments. There have been methods generated which lacked either sufficient throughput or chamber isolation and can potentially lead to metabolites and other secreted by products being transferred from one chamber to another. The system can be applied for screening studies with cells using the programmable and fully automatic microfluidic cell array that integrates on-chip cell culture with parallel on-chip generation of drug concentrations and pair-wise combinations. In this system, 1-100 cells are captured by different sets of configured pillars and are encapsulated by immiscible fluids as virtual wall in order to isolated different reactors.

SUMMARY OF THE INVENTION

In accordance with the present invention, there are provided methods for encapsulation of cells or molecules in trapping sites such as configured micropillars or micronozzles using immiscible fluids such as oil, fluorinert, oil containing surfactants, gel or other medium.

Still further in accordance with the invention, there are provided methods for multistep thermal cycling for PCR or other amplification by flowing of immiscible fluids as mentioned about at different temperature.

Still further in accordance with the invention, there are provided methods to guide the cells in to single cell trapping sites using pillars of smaller heights compared to the trapping pillars. The smaller guiding pillars will be immersed in to the oil during encapsulation of single cells.

Still further in accordance with the invention, there are provided methods for performing multistep chemical reaction using modified slip and lock chip.

Still further in accordance with the invention, there are provided methods for fabrication of the chips with microarray dried spots of primers or any other reagent or immobilized on semi-spherical gel on one layer and trapping of single cells with N sets of configured micropillars in another layer, where N can be 3 to 10 or more.

Still further in accordance with the invention, there are provided methods for the assay system for diagnostics in frequency domain by performing thousands of biochemical reactions and counting the positives for the quantification.

Still further in accordance with the invention, there are provided methods for performing additional movement of trapped picoreactor droplet using electrowetting on dielectric.

Still further in accordance with the invention, there are provided methods for carrying out electrophoresis in the medium of gel based immiscible fluids.

Still further in accordance with the invention, there are provided methods for preprocessing samples such as blood, tissue, tumors etc using cascaded magneto-diffusion or compounded flow focusing spiral inertial microfluidic based cell sorting.

Still further in accordance with the invention, there are provided methods for the formation of single cell encapsulated droplets or various molecules encapsulated droplets undocked from the trapping sites for further processing.

Still further in accordance with the invention, there are provided methods for separation or purification of constituents of the droplets such as mRNA or other species using magnetic beads through multistep processing of droplets such as cascaded fusion and fission steps.

Still further in accordance with the invention, there are provided microfluidic devices for carrying out the above-summarized methods. A microfluidic device of the present invention generally comprises a) at least 3-10 set of micropillars in a configuration to trap cells electrodes positioned parallel to the direction of flow, b) apparatus (e.g., on chip pump or micropumps) for applying a flow for oil and aqueous fluids and c) apparatus for measuring the biochemical reaction (e.g., fluorescent microcope, integrated fluorescence reader, other optical reader, GMR sensor, impedance sensor, nanosensor). (d) pair of electrodes to carry out electrophoresis in gel after amplification of molecules or genes (e) This device may comprise a microfluidic device that has a substrate layer and an upper layer, wherein the electrodes are located (e.g., fabricated, formed, affixed to or otherwise disposed on or in) one of the layers (e.g., on the substrate layer) and the microchannel is located (e.g., fabricated, formed, affixed to or otherwise disposed on or in) in the other layer (e.g., in the upper layer). The layers of the device may be fully or partially formed of different materials. For example, the layer in or on which the electrodes are located (e.g., the substrate layer) may comprise a glass and the layer on or in which the microchannel is located (e.g., the upper layer) may comprise a suitable polymeric material such as polydimethylsiloxane (PDMS), polycarbonate, polyacrylate, COC etc.

Still further in accordance with the invention there are methods to sort blood cells using with or with out magneto diffusion coupled cascaded diffusion channels for improved efficiency. The output of one diffusion channel will feed in to the input of the next diffusion channel. This cascade can form a circle or spirals with multiple turns with interconnected fluidics channels in spirals.

Still further in accordance with the invention there are methods to sort blood or multiple size or shapes using spiral fluidic channels with wider semi circular or rectangular flow focusing regions. The channel can be increasing or decreasing width gradient periodic pinching regions in spiral channel. The length or width of the pinching region can be increasing or decreasing gradient for different sizes of particle separation. Copy number analysis of single cell multiplexed QRT PCR is used for quantification of CTC based cancer diagnostics.

Still further in accordance with the invention there are methods to perform programmable array of living cells using multiple micropillars arranged in a form of a perforated cup with funnels for collecting the cells and reactor for performing cell based assay. Such arrays of reactors are isolated from one another by flowing immiscible fluids. Combinatorial drugs and several cocktail ingredients can be flowed to the array using diffusion based gradient generators. The volume of such reactors can be adjusted by increasing the circular arrangement of the pillars. Sufficient nutrients and fluorescence probes are added to the reactors before starting cell growth/death monitoring in cell based assays.

Still further in accordance with the invention there are methods to completely isolate cells from immiscible fluidics by another concentric layer of pillars. The inner pillars are arranged with smaller distance apart while the outer pillars are arranged with larger distance apart. The cells are trapped in the inner pillars while the cells escape out of the outer pillars. The flow rates of the fluidics between 0.1 uL/min and 10 uL/min are responsible for the formation of the reactors.

Further aspects, elements and details of the present invention are described in the detailed description and examples set forth here below.

BRIEF DESCRIPTION OF THE DRAWINGS (FIG. 1A) The concept of picoreactor based single cell trapping, encapsulation and gene expression profiling chip/system. Multiplexing of PCR is accomplished using Microarray spotting of primer pairs on the bottom layer the chip in a set arranged spatially before assembling the device. (FIG. 1B) The chins with fluid circuits are configured to trap single cells in micropillar array system, (FIG. 1C) The chips with fluid circuits are configured to encapsulate single cells using immiscible microfluidics, (FIG. 1D) The chips with fluid circuits are configured to perform RT-PCR in a two-dimensional array (FIG. 1E) The chips with fluid circuits are configured to rapidly analyze PCR or gene expression results for clinical diagnostics or biomedical research.

FIG. 2. (A) Successive frames of the formation of encapsulated reactors. FIG. 2(B) Successive frames of thermal cycling profile FIG. 2(C) Velocity of flow profile inside the chip (The arrows points to the direction of the flow) FIG. 2(D) Kinetics of temperature profile during heating and FIG. 2(E) Kinetics of temperature profile during cooling FIG. 2(F) 3-d schematic of flow showing cells trapped at the micropillar trapping sites in a compartment of the single PCR chip FIG. 2(G) Additional pillars are shown as guidance for the cells in to the trap sites.

FIG. 3. (A) Single cell trapping array on configured pillars in an array of compartments FIG. 3. (B) Single cell on trapping sites FIG. 3. (C) Single cell encapsulation sites.

The steps of cell trapping and encapsulation for single cell PCR are FIG. 4. (A) Oil flow after cell trapping for encapsulation. FIG. 4. (B) Thermal cycling: flow of hot oil. FIG. 4. (C) Thermal cycling: flow of cold oil. FIG. 4. (D) Real time PCR with fluorescent imaging.

Figures 4A, 4B, 4C, 4D:
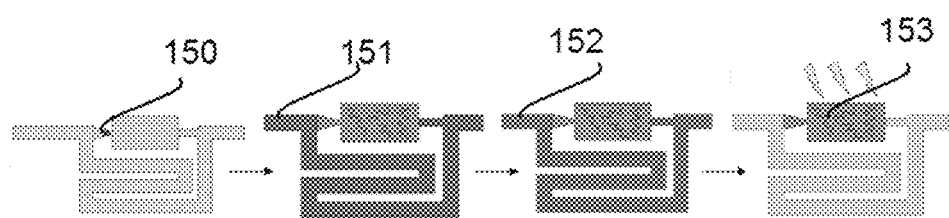
Figures 4E, 4F, 4G:
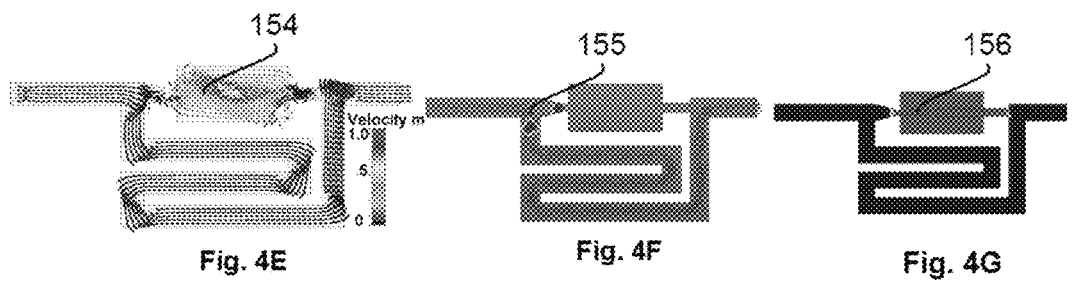

CFD flow analysis in a compartment of micronozzle cell trap chip. FIG. 4. (E) Velocity profile of fluid flow after formation of single cell encapsulated reactors. FIG. 4. (F) Single cell trapping and flow blockage for successive cells. FIG. 4(G). Encapsulation of single cells with oil FIG. 4(H). Temperature profile of oil after FIG. 4. (I) 0.01s, FIG. 4. (J) 0.1 s and FIG. 4. (K) 0.25 s.

FIG. 5 (A) Representation of encapsulation of a single cell trapped by a configured array of 6 micropillars. FIG. 5 (B) In-situ electrophoresis after PCR amplification in gel medium from the picoreactor site using a pair of electrodes fabrication on the bottom glass substrate. FIG. 5 (C) picoreactor droplet is coupled with EWOD to move the single cell encapsulated droplet for further serial processing.

FIG. 6 Fluidics of the massively parallel picoreactor chip for homogeneous cells capture in each compartment. The cells and reagents are flowed from the top inlet. Extra cells or cell clusters adhered weakly near the trap sites are cleaned by the flow at the side inlet.

FIG. 7. (A) Mechanical design for 'slip and lock' stage movement during fluidic delivery. FIG. 7. (B) Fluidics operation of slip and lock Chip (side view). FIG. 7. (C) Fluidics operation of slip and lock Chip (top view).

FIG. 8. (A) Single cell diagnostic system with fluidic manifold with embedded chip for performing high throughput single cell PCR. Immiscible fluids from hot bath and cold bath are circulated to perform thermal cycling. A set of pin valve at the chip enable cells flow and thermal cycling sequentially (H—hot bath, V—valves, C—Cold bath, W—waste chamber). FIG. 8. (B) Fluorescent imaging system for quantifying clinical diagnostics.

FIG. 9. (A). The diagram shows the mechanism of fluorescent RTPCR. FIG. 9. (B) The diagram shows the multiple fluorescence imaging on a the chip highlighting positive responses to multiplexed RT-PCR FIG. 9. (C) Complete steps of CTC diagnostics system.

Figure 10:
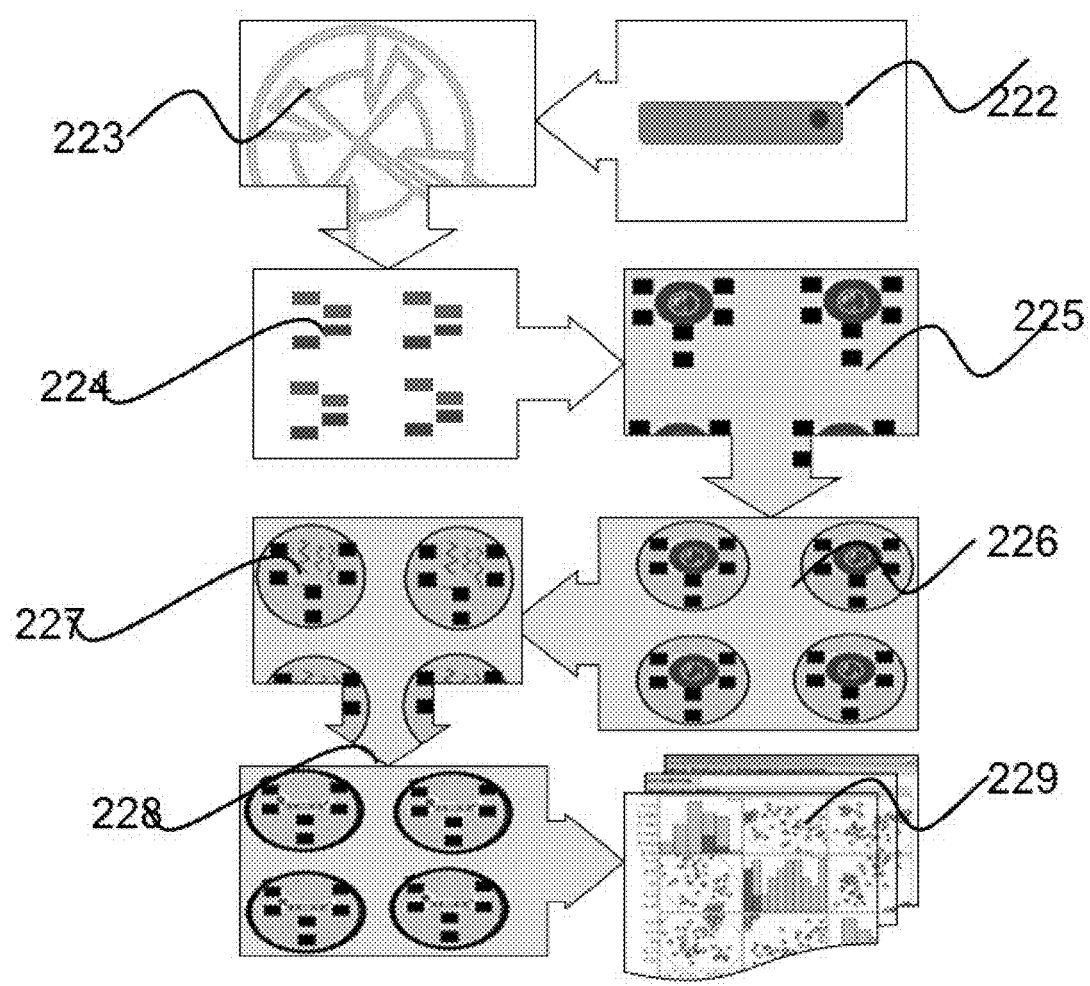

FIG. 10 Operation of Single cell PCR using blood lymphocytes.

Figure 11:
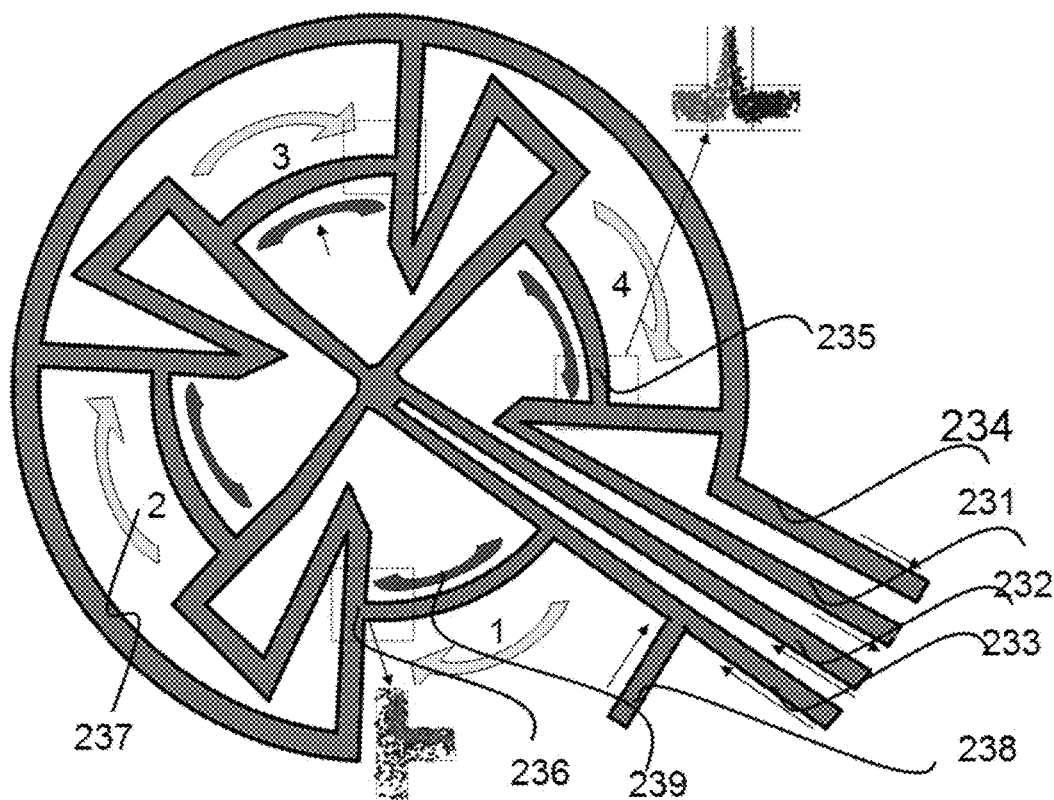

FIG. 11 The diagram shows the concept of the chip/system for magneto-diffusion based lymphocyte separation from whole blood.

FIG. 12 (A). Inertial fluidics devices based on high aspect ratio spiral channels with wider semi circular flow focusing regions for the isolation of larger cells from whole blood. (B). CTC enrichment from whole blood using decreasing width gradient periodic pinching regions in spiral channel inertial fluidics.

FIG. 13. (A) Five serial steps of mRNA linear amplification using flow of picoliter droplets (B) Fluidics for continuous droplet based mRNA purification using magnetic beads driven by magneto-fission and fusion of droplets.

Figure 14A:
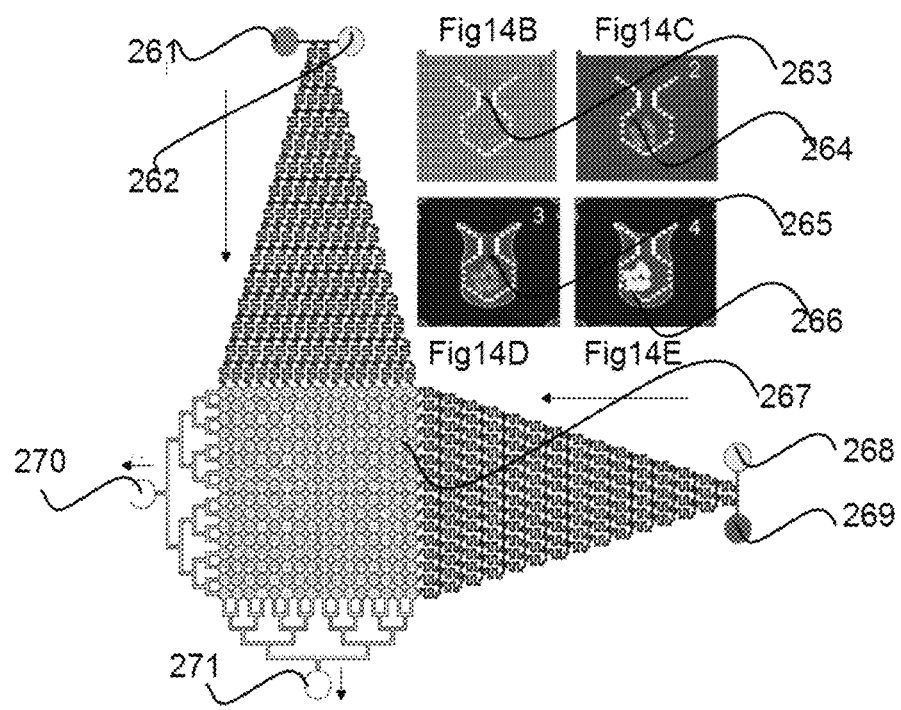
Figure 14F:
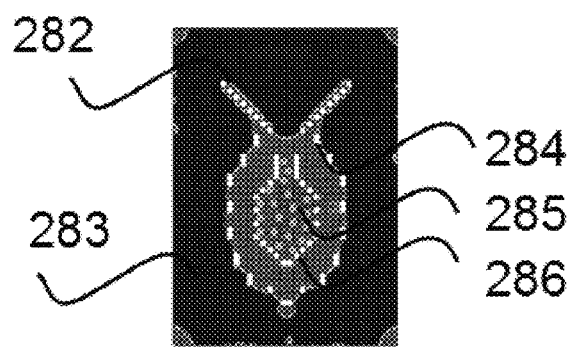
Figure 14:
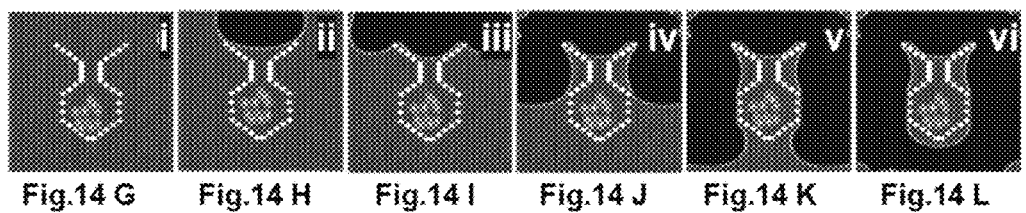

Conceptual Diagram of Programmable Array of Living cells system. FIG. 14 (A) Full Chip with fluidic operations illustrated in the in-pictures. FIG. 14 (B) Flow of cells through the chip to trap cells at the 'cup' shaped reactor FIG. 14 (C) Flow of buffer to clean up the cells in the channels and incubation with combinatorial drug. FIG. 14 (D) Flow of oil to form cells encapsulated reactors FIG. 14 (E) Cell culture with periodic florescence imaging for cell growth monitoring FIG. 14 (F) Improved design featuring complete isolation of cells from immiscible fluidics. Time lapse frames FIG. 14(G-L) of aqueous cells in compartments isolated by virtual walls.

DETAILED DESCRIPTION AND EXAMPLES

The single cells or molecules encapsulated picoreactors chip/system as shown in FIG. 1A to FIG. 1E for gene amplified enumeration and/or followed by electrophoresis is critical to the development of pathology, oncogenesis, and other processes of a desired target cell or molecules. The system combines single cell trapping in micropillars 100, immiscible microfluidics 101, flow based thermal cycling from hot 102 and cold 103 reservoirs and fluorescent reverse transcription (RT)-PCR 104 technologies performing molecular diagnostics in a quick, high-throughput, and cost-effective fashion.

This highly integrated platform is configured to:
precisely trap a single cell in array of configured micropillars 105;
encapsulation of single cells as picoliter reactors using immiscible microfluidics;
simultaneously perform thousands of single-cell PCR in picoliter volumes 106;
rapidly analyze the PCR results on a chip; and
analyze single-cell of large populations for clinical diagnostics or biomedical research.

The combination of high-fidelity manipulation of single cells and the ability to perform nucleic acid amplification offers the possibility of developing powerful automated instruments.

Chip Design and Microfluidic Modeling:

Using computational fluid dynamics (CFD) simulations, we have proved that the picoliter reactor can form around trapping sites using immiscible fluids. FIG. 2A shows successive frames of the formation of encapsulated reactors. The aqueous phase 120 is encapsulation 121 by the flow of oil phase. In another simulation the oil at 30 deg 122 is increased to 90 deg 123. The successive frames of thermal cycling profile is shown in FIG. 2B. In order to study the efficiency of trapping of cells, the flow profile at the traps is studied. The velocities are lower 125 at the traps compared to the inlet 124 and between the traps. The velocity of flow profile inside the chip is shown in FIG. 2C. Further kinetics of temperature profile during heating 126 and cooling 127 are shown in FIG. 2D and FIG. 2E respectively. Different curves represent the number of points monitored at the different positions in the direction of the flow of oil. 3-d schematic of flow showing cells trapped 130 at the micropillar trapping sites 131 in a compartment of the single PCR chip is shown in FIG. 2F. FIG. 2G represents an improved design using guiding pillars 132 that focuses the cells to trap them. The geometry and dimension of the channel, the flow parameters for aqueous and oil flow, and electrical parameters for the droplet sorting and fusion are optimized. Further the flow rates for oil and aqueous media and temperature behavior for thermal cycling are optimized using the CFD-ACE+ multiphysics modeling tool, which solves the Navier-Stokes equation for flow along with "Volume of Fluid" modeling for immiscible fluids and Gauss equation using the following set of equations:

$$\frac{\partial(\rho u)}{\partial t} + \nabla \cdot (\rho \vec{V} u) = \frac{-\partial p}{\partial x} + \nabla \cdot (\mu \nabla u) + S_M$$

$$\frac{\partial F}{\partial t} + \nabla \cdot \vec{v} F = 0$$

where r is density, p is pressure, S is source term, µ is viscosity, u—velocity, F is the liquid volume fraction of secondary fluid, and v is the velocity vector.

Figures 3A, 3B, 3C:
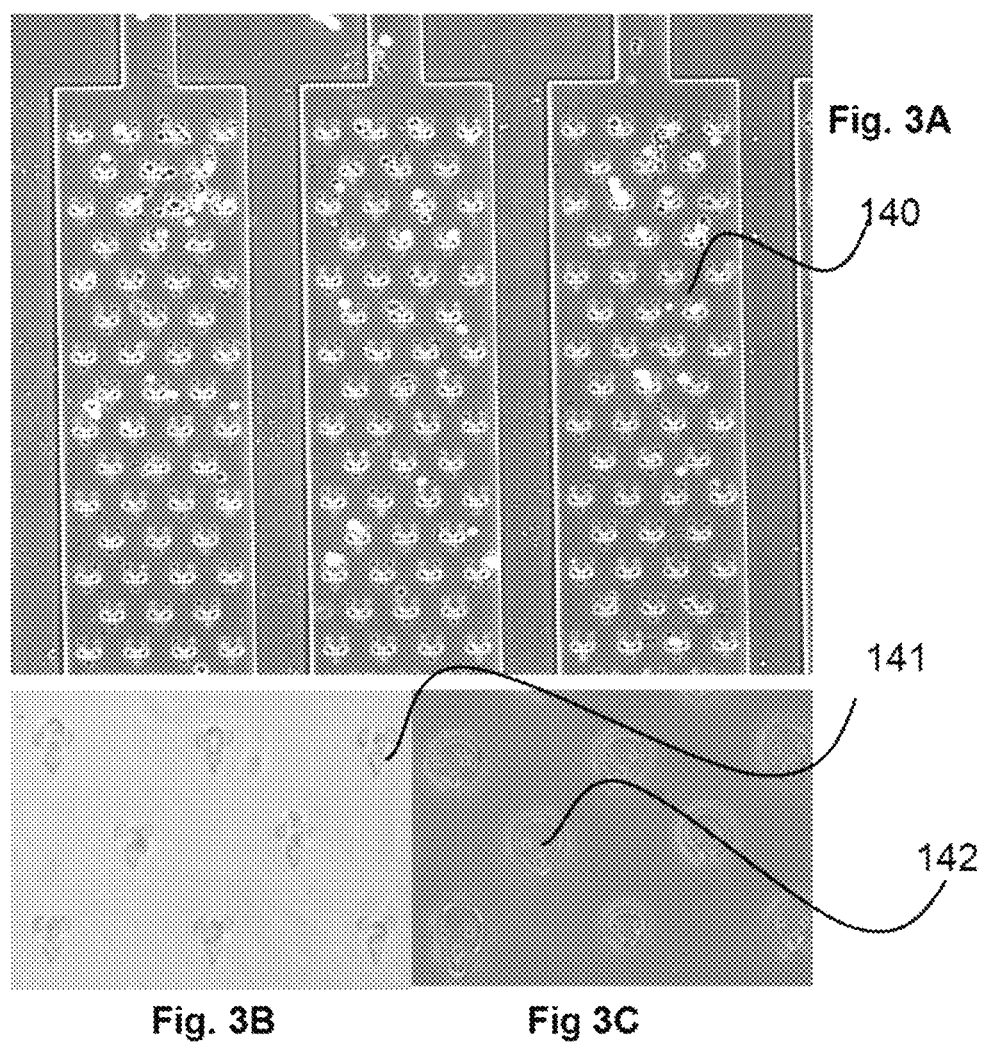

Single Cell Trapping Sites:

There are a few mechanisms of trapping sites for single cells. In one case as in shown in 105, each single cell trapping site is configured by six square micropillars of dimension 5 um×5 um is arranged so that a 10-15 um cell enter and get trapped while the fluid flows away. Additional micropillars are added to increase the volume of PCR mix solution in each reactor site. The $6^{th}$ micropillar at the bottom is added to increase the volume of the encapsulated PCR solution as well as for the smooth formation of droplet. Different types of configuration constituting 3 to 10 or more pillars have been used to trap single cells and to encapsulate sufficient amount of fluids around the single cell. The pitch of the trapping sites are optimized with different pitch in the x and y directions. Lesser the distances the yield of trapping of the cells is better. If the distance is too small there is chocking of cells in the channel. If the distances are more the cells freely flow through the device to the outlet and trapping is limited. Additional pillars (FIG. 2G) for guiding 132 the cells in to the single cell trap sites are used to enhance the single cell trapping efficiency. These pillars are shorter so that they will not allow clustering or aggregation of cells and will be immersed in the immiscible fluid during the encapsulation of the single cell. FIG. 3A shows the trapping of single cells and the complete device formed by an array of compartments in a 2-d array. Inside each compartment a 2-d array of trapping sites 140 are formed in a triangular lattice. Trapping of cells 141 and encapsulation using oil 142 are shown in FIG. 3B and FIG. 3C.

Figures 4I, 4J, 4K:
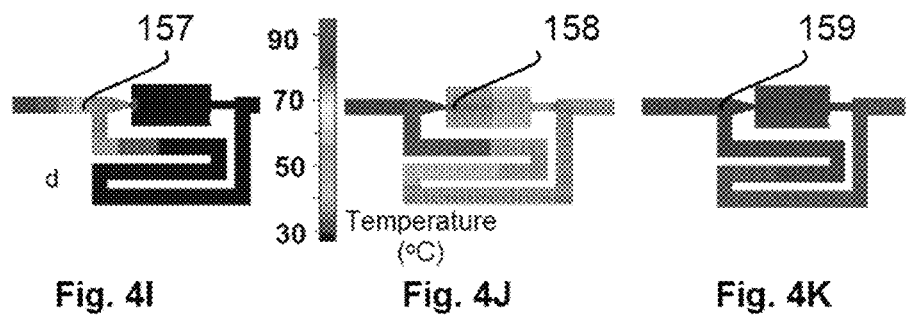
Figures 5A, 5B, 5C:
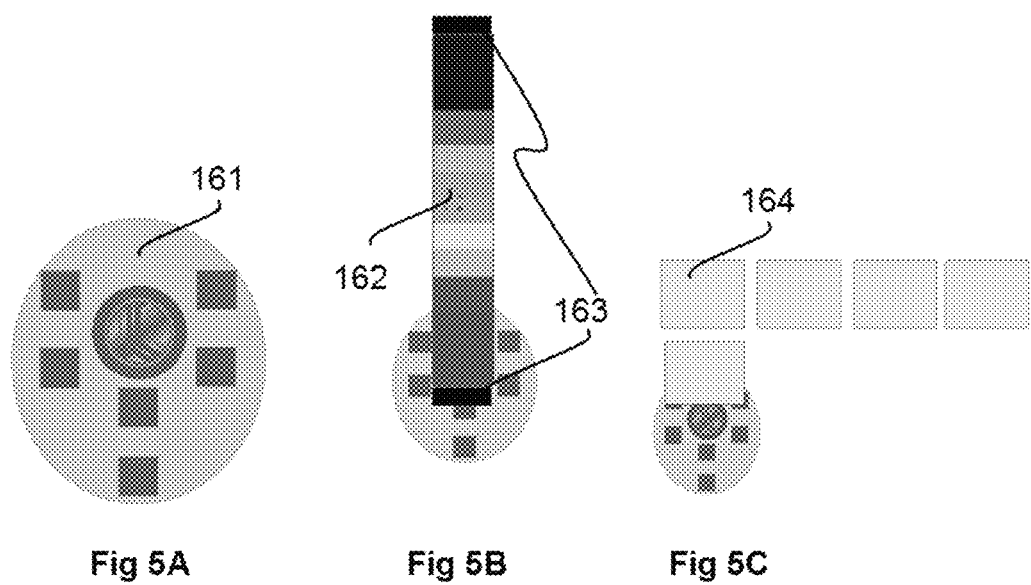

In another method each single cell trapping site is configured by a 5 um nozzle in the microchannel and many such trapping sites are connected in series and parallel throughout the channel. FIG. 4A-FIG. 4D shows single cell trapping at the nozzle 150 followed by oil encapsulation and thermal cycling using flow of hot 151 and cold 152 oil for RTPCR fluorescent imaging 153. FIG. 4E shows the results of velocity profile 154. The single cell trapping sites offer blockage 155 to the flow (FIG. 4F) and successive cells in the direction of the trapped cell. The cells are trapped as they pass through the lower flow resistance or shorter channel. The trapped cells are valved so that successive cells flow through the longer channel. The number of the trapping sites in series and parallel are optimized with the calculation of the pressure due to the flow of oil and the pump used. The sample with disaggregated cells is loaded into the cell inlet in the microfluidic chip and is split in to many channels using binary splitters. The cells are equally split in all the splitter channels. The cells from splitter channels enter in to the trapping sites and finally merge in binary merger channels to the outlet. The number of cells exiting the outlet is the difference of the cells at the inlet and the number of cells trapped. FIG. 4.G shows the reactor 156 after the flow of oil. In a 1"×3" area, ~10000 sites can be accommodated along with other channels for fluidic delivery. The temperature profile of kinetics during thermal cycling using oil after 0.01 s (FIG. 4I), 0.1 s (FIG. 4J) and 0.25 s (FIG. 4K) is shown. The temperature increased from 30 deg 157 through 70 deg 158 to 90 deg 159 respectively. FIG. 5A shows a single trapping site 161 and possible electrophoresis (FIG. 5B) for the mobility of nucleic acids 162 using a pair of electrodes 163. Further processing of the PCR products are carried out through EWOD activation of droplets (FIG. 5C) after PCR experiments using surface electrodes 164.

Splitter/Merger Channels to Compartments and Cleaning:

The sample with disaggregated cells and PCR solution is loaded into the cell inlet in the microfluidic chip and is split in to many channels using binary splitters as shown in FIG. 6. The cells are hydrodynamically flowed 172 along with PCR master mix and primers. The cells are equally split in all the splitter channels. The cells from splitter channels enter in to the trapping site compartments in a parallel fashion. Flow of fluid and cells enter in to serial compartments and finally merge in binary merger channels to the outlet. The number of cells entering the outlet is the difference of the cells at the inlet and the number of cells trapped in micropillar sites. Compartmentalizing the trapping sites improves the homogeneity of the flow of cells within the trapping sites 173 so that the yield of single cell trapping is improved. Placing the compartments serially in a serpentine channel increases the fluidic resistance of the channel. So the flow of cells in the chip is divided in to many subchannels using binary splitters and the compartments are arranged in a parallel fashion. The maximum number of trapping site in a compartment is limited by the parabolic fluidic flow. We have observed in the CFD simulation that a maximum of 4 trapping sites are configured in the direction perpendicular to the flow. It is also necessary to add sufficient margin in the compartment in all sides for placing the trapping sites. The number of trapping sites on the direction of the flow is limited by the cell density. In a 10 mm×10 mm area, ~10000 sites can be accommodated.

An extra fluidic channel on the left inlet 170 is used for cleaning weakly adhered cells near the trapping sites so as to enhance single cell encapsulation. Other PCR reagents are flowed after the cleaning of the channels.

Slip and Lock Chip for Single Cell PCR:

The PCR reagents is flowed through the top plate 180 and is placed onto the bottom plate 181 in a air tight locked position secured using a Z-stage as shown in FIG. 7A or using electromagnetic based locking system. The ducts in the bottom plate were overlapped with the empty wells in the top plate, forming a continuous fluidic path for loading of the sample. The bottom plate has channels for single cell trapping followed by the flow of oil. Fluorinert is the oil used for the operation of slip chip. Since the surfaces of both plates are hydrophobic and fluorophilic, a thin layer of fluorinert is trapped between both plates. The top plate was then moved 182 using an X-stage relative to the bottom plate as shown in FIG. 7B to align the PCR reagent containing wells in the top plate with the single cell reservoirs in the bottom plate. Once the Slip and Lock Chip is aligned, the PCR reagents and the single cells in both plates are mixed by diffusion. After the mixing, the chip is locked in place using the Z-stage and thermal cycling for PCR is started. The slip and lock chip is configured to perform five serial steps (I) Flow of cells through the chip traps single cells at the trapping sites 185 (II) Flow of oil to form single cell encapsulated plugs/reactors 186 (III) Flow of lysis buffer, PCR mix and primers through the slip chip 187 (IV) slipping and locking of Slip Chip for mixing the reagents with single cells 188 (V) Single cell PCR thermal cycling for amplifying gene and Fluorescence detection 189 for quantifying diseases. Fluidics operations of slip and lock Chip are shown in FIG. 7C (side view) and FIG. 7D (top view). The operation steps are (i) Flow of cells 196 for trapping and valving 191 of single cells (ii) flow of oil 197 to encapsulate 193 the single cell (iii) Flow of cell lysis/PCR master mix 194 solutions (iv) Slipped chip 197 to flow the add the reagents for PCR reaction 195. The pressurized flow of reagents is accomplished by locking 198 the chip in position. The flow rate or pressure is adjusted with trial experiments to avoid any leak in the slip chip during thermal cycling. After the delivery of lysis buffer the cells are lysed and are de-valved at the nozzle. This develops a flow towards the reservoir area and so the DNA materials homogeneously mix with the PCR master mix and the primers. Moreover, the continuous flow of thermal cycling oil around the reactor keeps the PCR mixture in the state of convective mixing.

Chip Micro Fabrication:

The channel is fabricated from a SU8 mold of height 5-20 μm using standard PDMS techniques depending upon the size of the cells in experimentation. The fresh surface of PDMS is treated with oxygen plasma for bonding with the glass plate. The microfluidic channel is made hydrophobic. Once the channel and micropillar geometries are optimized the chips are manufactured in a large scale using injection molding using a master.

Soda-lime glass plates with chromium and photoresist coating is used for fabricating devices. Microchannels and wells on the glass plates are made by using standard photolithographic and wet chemical etching techniques. The dimensions of the wells is 50 μm×100 μm laterally and 50 μm in depth. The surfaces of the etched glass plates is cleaned and subjected to an oxygen plasma treatment, and then the surfaces is rendered hydrophobic by silanization in a vacuum desiccator as described. The channel with trapping sites are fabricated using SU8 and is used together. The channel width is 20 μm and the trapping nozzle is 5 μm. The reservoir for the single cell PCR is 50 μm×100 μm.

Figure 8A:
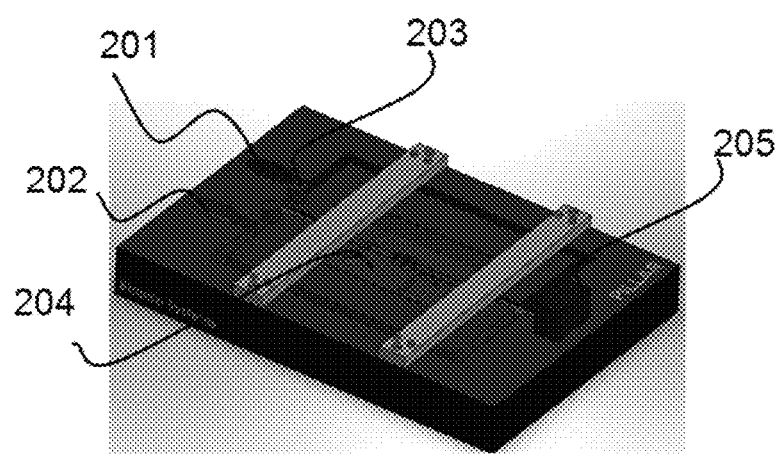
Figure 8B:
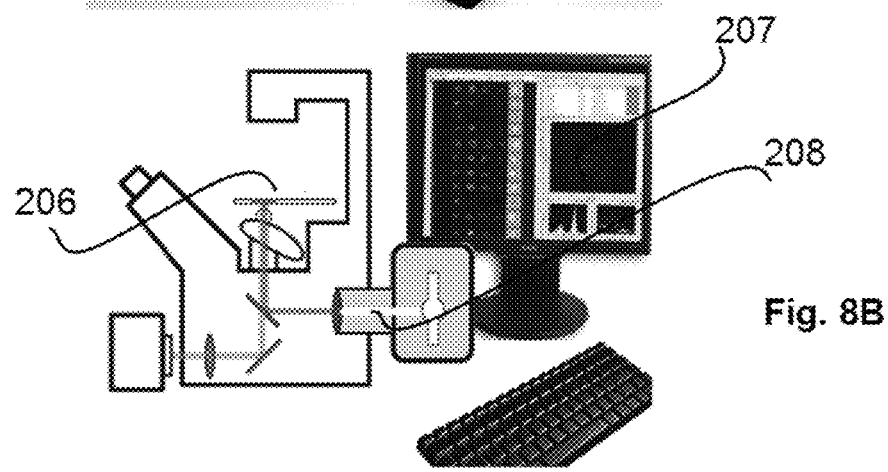

Chip Operation:

The chip (as shown in FIG. 1A to FIG. 1E) is configured to perform five serial steps (1) Microarray spotting of multiple primer pairs, (2) Flow based single-cell trapping using micropillars, (3), Flow of immiscible fluid for forming picoliter reactors (4) convection driven thermal cycling for PCR, and (5) Fluorescence imaging based quantification and deletion analysis. The sample of disaggregated cells along with PCR master mix and PCR solution is loaded into the 'cells inlet' in the disposable microfluidic chip which sits on to the 'fluidic manifold' as shown in FIG. 8A. The manifold accommodates two oil baths—cold 201 and hot 202, valves 203 and a pump 205 for oil delivery in to the disposable chip 204. The sample cells flow is split in to many channels and each single cell is trapped at the micropillars trapping sites. The trapped single cells is encapsulated by flowing oil at RT from cold bath and the oil flow front goes around the micropillars as shown in the CFD simulation. The encapsulated reactor consists of single cell, spotted PCR primers and encapsulated PCR master mix with lysing buffer and enzymes. In order to perform PCR thermal cycling oil from isolated hot and cold baths is heated at temperatures 95° C. and 50° C. and is circulated into the entrapped droplets alternately using the pump. We have tested with CFD simulations that the sealed picoreactors locked at the micropillar sites is immobile with temperature or pressure effects. A heating rate of 1° C./ms and a cooling rate of 2° C./ms are expected during the thermocycling with the circulation of oil. The fluorescence detection system consists of a tungsten-halogen/mercury lamp 208 as an excitation source and a CCD detector with an XY stage 206 as shown in FIG. 8B. After loading the cells and reagents, the chip is operated automatically using Labview software through NI-DAQ interface for final fluorescence analysis 207 of the multiplexed PCR and further diagnostics of several diseases.

System Integration:

The system consists of a flow device, fluorescence detection, thermal cycler, and software control systems. The flow device is facilitated with Pico syringe pumps (Harvard Apparatus, MA) for delivering fluids into the channel with a constant flow rate between 10 μl/min and 100 nl/min. The PCR is performed using an externally applied programmable Peltier heater. A Peltier heating element (Melcor) controls the nanodroplet temperature between 30 and 95° C. A heating rate of 6-8° C./s and a cooling rate of 2-4° C./s are expected. The timing of the thermal cycling (94° C., 60° C., and 72° C.) is also controlled by the software. The fluorescence detection system consists of a tungsten-halogen lamp as an excitation source and a CCD detector (Spectral Instruments Inc., Tucson, Ariz.). Various optical filters are used to accommodate for different fluorescence dyes. The common dyes are FAM, VIC, TAMRA, SYBR Green, JOE, etc. The wavelengths of excitation light are 470 nm, 490 nm, 530 nm, and 635 nm. Since the fluorescence signal is amplified, the CCD has sufficient sensitivity for fluorescence detection. If the array area is too big (>1 cm$^2$) for single illumination, a scanning mechanism is facilitated for multiple illuminations.

Figures 9A, 9B, 9C:
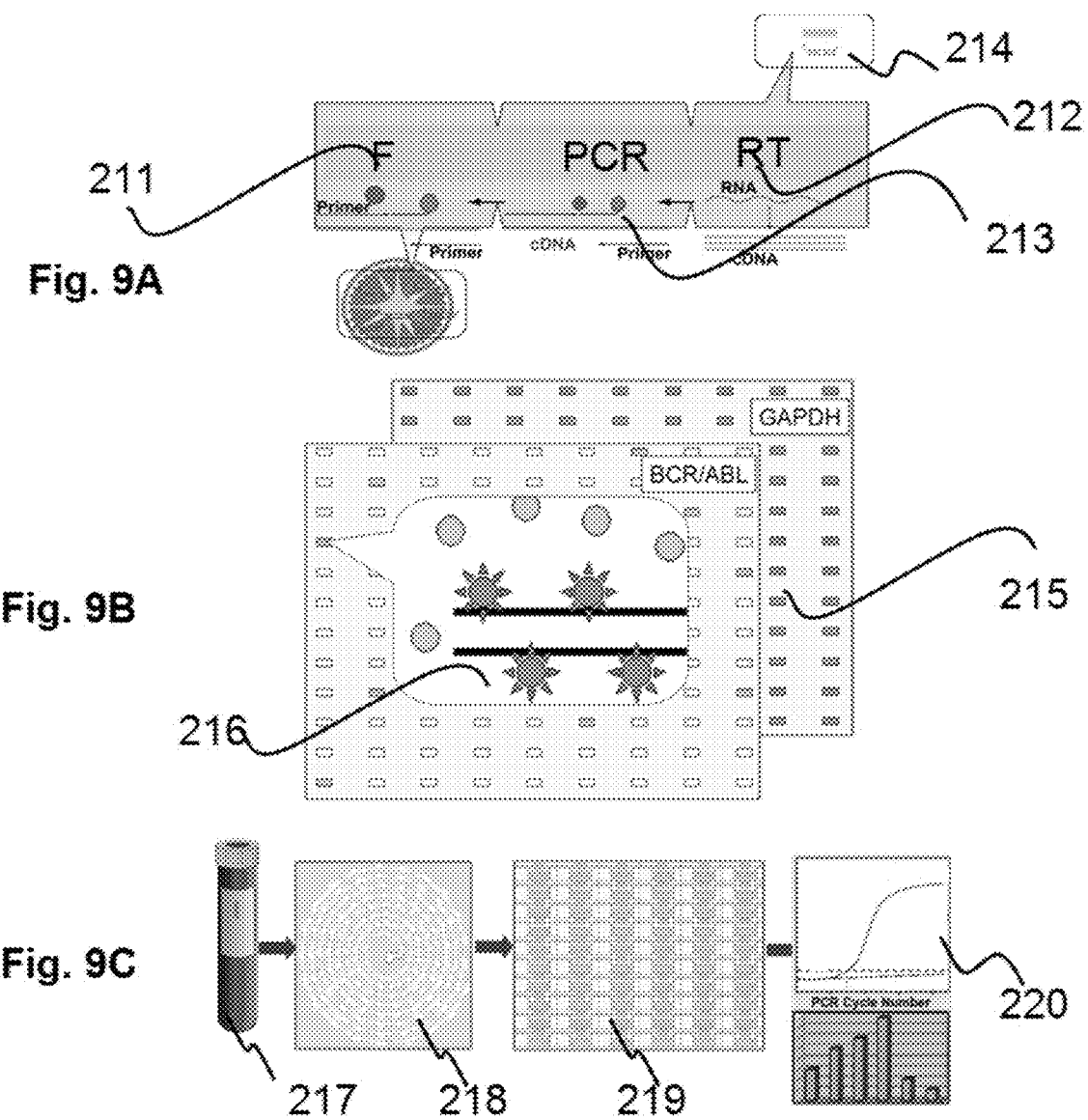

All the components are programmed using Labview software through NI-DAQ interface. After loading the cells and reagents, the chip is operated automatically for single-cell encapsulation, generating PCR samples, performing temperature control for PCR cycles and final fluorescence analysis of the PCR data. FIG. 9A shows the shows the mechanism of fluorescent RTPCR where RNA 214 is translated to cDNA using reverse transcripase 212 and amplified using primers 213 to give fluorescent signals 211. The diagnosis of diseases are carried out by the analysis of fluorescence signal 216 with positive response from multiplexed qPCR with control 215 as shown in FIG. 9B. This system can be used for analysing circulating tumor cells (CTC) found in blood for patients with minimum residual diseases. A schematic of CTC diagnostics steps using copy number variation analysis is shown in FIG. 9C. The system takes blood samples 217 in the input and performs single step CTC enrichment using periodic pinching regions in high aspect ratio spiral channel 218 and high throughput single cell trapped picoreactor 219 encapsulated Q-RT PCR Followed by analysis through copy number variation 220.

Preprocessing for Clinical Samples:

The scheme for the diagnosis of clinical samples 222 using gene expression profiling is shown in FIG. 10. The chip with fluid circuits are configured to Lymphocytes purification 223, Microarray spotting of multiple primer pairs 224, Flow based single-cell trapping using micropillars 225, Flow of immiscible fluid for forming picoliter reactors 226, convection driven thermal cycling for PCR 227, and Fluorescence imaging 228 based quantification and analysis 229 of positive genes. In FIG. 11 the concept of the magneto-diffusion based lymphocyte separation from whole blood is described. The whole blood is delivered in to the chip in one channel 233 and reagents in another channel 232. The lymphocytes are separated 234 from waste 231. This chip sort blood cells using with or with out magneto diffusion coupled cascaded diffusion channels for improved efficiency. The output of one diffusion channel will feed in to the input of the next diffusion channel with the direction shown 237. Separation of cells are partially accomplished in the first iteration 236 and well accomplished at the final iteration 235. These cascaded channels can form a circle or spirals with multiple turns and interconnected fluidics channels in spirals. The refined lymphocytes are carried to the next stage and finally send to the purified outlet for genetics or epigenetics information processing.

Figure 12A:
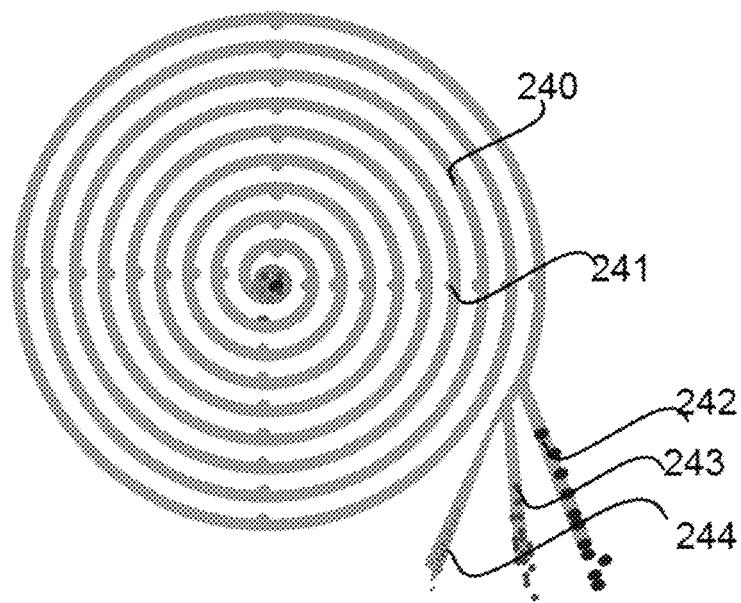
Figure 12B:
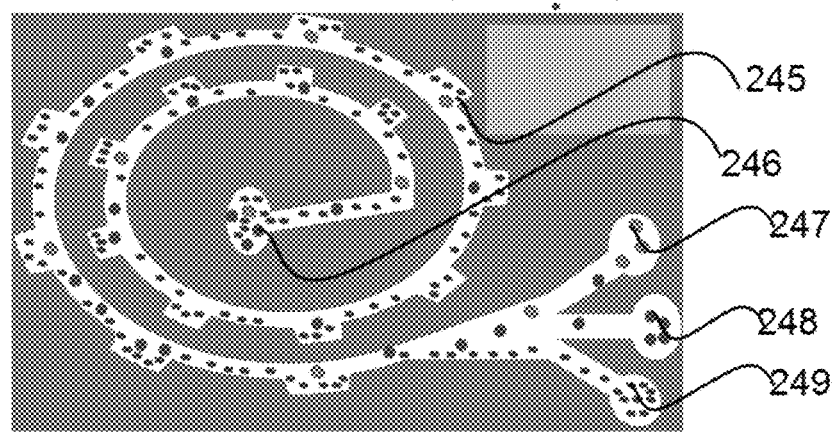

Further inertial fluidics manipulation is utilized to isolate larger cells such as CTC from whole blood as shown in FIG. 12A. In this system high aspect ratio spiral channels 240 with wider semi circular 241 flow focusing regions are utilized to sort the cells as shown in FIG. 12B. The pitch and width of the flow focusing channels are varied to design the spiral channels in a linear, exponential or power series in order to optimize the sorting efficiency and specificity. CTC 242 is separation from PBMC 243 and RBC 244 cells. In a special design as shown in FIG. 12B, CTC enrichment is accomplished from whole blood 246 using decreasing width gradient periodic pinching regions 245 in spiral channel inertial fluidics. Different sizes of cells such as CTC 247, PBMC 248 and RBC 249.

Figure 13A:
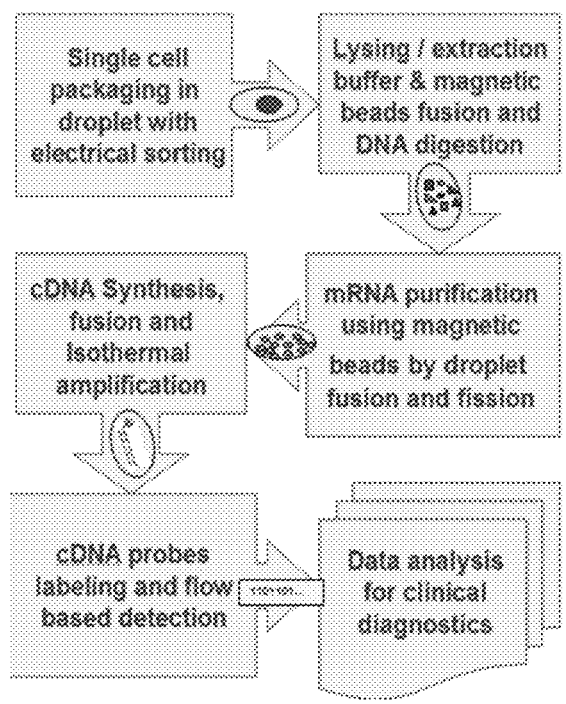

Post-Processing of Docked Picoreactor:

Using 'electrowetting on dielectric' (EWOD), the docked picoreactors in trapping sites with single cell encapsulation can be moved for further serial or multistep processing. In order to accomplish the movement of such droplets, EWOD electrodes assembly is laid on the bottom layer of the chip as shown in FIG. 5C. Further, thousands of such droplets can be collected at an outlet and they can be further processed separately. FIG. 13A show five serial steps of mRNA diagnostics using flow of picoliter droplets and the fluidics for continuous droplet based mRNA purification using magnetic beads.

Figure 13B:
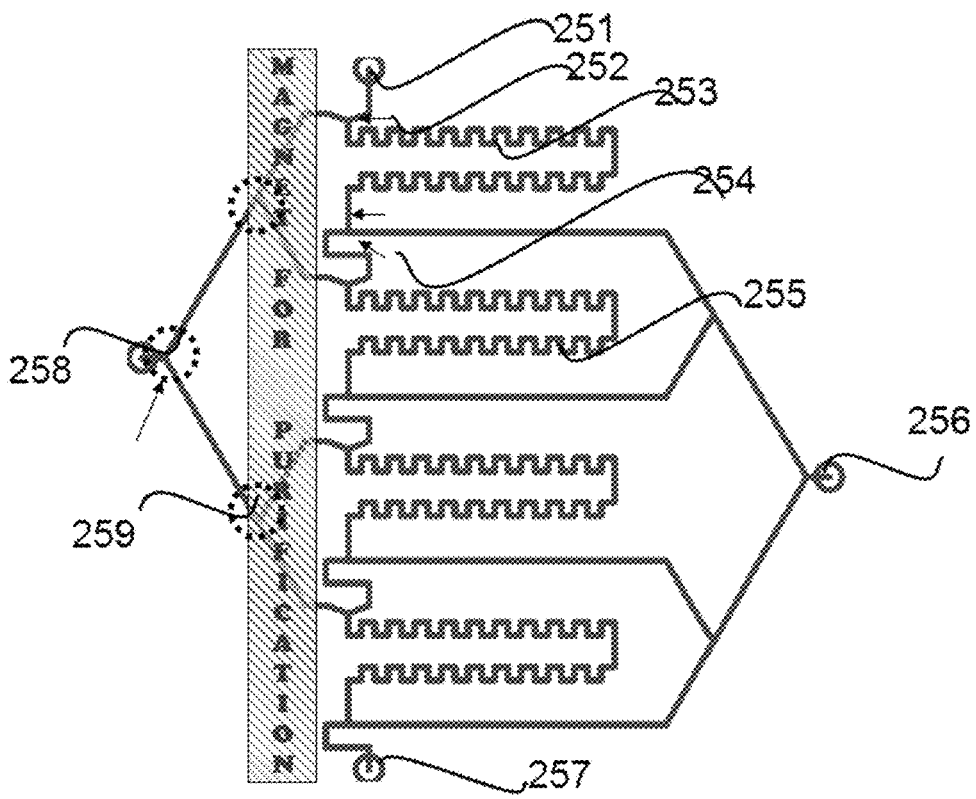

In this purification chip shown in FIG. 13B, the droplet carrying lysed cell with mRNA-polyA bound on the magnetic beads with polyT enters at the inlet 251. The droplet is washed in a few stages using wash buffer droplets. The washing step consists of droplet fusion at the bifurcation junction 252 to fuse wash buffer droplets, mixing loop 253 to homogenously mix the wash buffer with the lyzed cell ensemble, magnetic separation channel and finally droplet fission 254 to remove the other materials from the droplet. The magnetic beads within a droplet are polarized by the strong magnet on one side of the chip. The fission on the droplet separates the droplet in to two parts: one containing the magnetic particles and other with the wash buffer waste. Several stages 255 of washing are required to completely remove the other cell products from the magnetic beads. The chip performs 4 stages of washing. The wash buffer droplets 258 for every stage is supplied by separate channels using a serial droplets to parallel droplets converting channel network based on binary sorting or flip-flop bifurcation channels 259. The mRNA is eluted with an elution droplet and is binary split to remove the magnetic beads using a droplet fission chip with elution buffer droplets and mRNA bound magnetic beads droplets as inlets.

Programmable Array of Living (PAL) Cells:

The PAL chip will be designed for combinatorial fluidics for 16×16 cell based assay reactors. This design will enable us to perform 2 drugs at 16 concentration or 4 drugs (261, 262, 268, 269) at 8 concentrations for combinatorial drug screening. In this PAL system, ~100 cells are captured by cup shaped pillars 263 and are encapsulated 265 by immiscible fluids as virtual wall in order to isolated different reactors for cell growth monitoring under the influence of TRAIL sensitizer drug cocktails 264. The PAL system (as shown in FIG. 14A) is configured to perform four serial steps (I) Flow of cells to fill the 'cup' shaped reactor (FIG. 14B). (II) Flow of buffer for cells cleanup and flow of combinatorial drug (FIG. 14C). (III) Flow of oil to form cells encapsulated reactors (FIG. 14D). (IV) Cell culture with florescence imaging based cell growth monitoring (FIG. 14E) 266. In the single layer pillars design, the immiscible fluid is very close to the cells. The immiscible fluids such as fluorinert is biologically inert and may not interfere with the cell membrane. However, a double layer pillars (as shown in FIG. 14F) can encapsulate cells only in the inner layer of the reactor for 24-72 hours of cell based assay experiments. The inner layer pillars 286 will be designed with smaller (~5 um) spacing while the outer pillars 284 will be designed with larger (10-20 um) so that the cells 285 are captured only in the inner compartment. The outer layer pillars can encapsulate sufficient cell media/nutrition for continuous culture for several days. A focusing set of pillars 282 guide the cells in to the capturing reactor. This design also features an overflow "cup" arrangement for the cells at the top of the inner layer pillars. The gap between the funnel and the cup will be optimized to avoid any clogging of cells. This design will ensure that equal amount of cells will be captured in each reactor. The time lapse frames of single layer design with aqueous cells in compartments isolated by virtual walls are shown in FIG. 14G-FIG. 14L.

Example 1: Diagnostics of Prenatal Diseases

The system is used for various genetic diseases or syndrome at prenatal diagnosis. For example, muscular dystrophy refers to a group of more than 30 genetic diseases that involve mutations in any of the thousands of genes that program proteins critical to muscle integrity resulting degeneration of skeletal muscles towards death. Duchenne Muscular dystrophy (DMD), caused primarily by intragenic deletion or duplications has no treatment as of now and prenatal diagnosis is the most important preventive strategy. DMD alone affect approximately 1 in every 3,500 to 5,000 boys or between 400 and 600 live male births each year in the United States. Detection of a DMD gene mutation is sufficient to establish a diagnosis of DMD and so multiplex PCR method is the best diagnostic tool owing to its characteristics such as specific, accurate, sensitive and rapid. Presently, the prenatal diagnosis of DMD is performed through deletion analysis using DNA extracted following amniocentesis or chorionic villous sampling (CVS).

After sampling, CVS are microscopically dissected and after homogenization, DNA is extracted and controlled with multiple polymorphic markers to ensure its fetal origin and to avoid maternal tissue contamination, which could possibly result in inaccurate results. The massively parallel microspatially addressed multiplexed PCR system performs fast frequency domain sample analysis of DMD from prenatal samples at high reliability, accuracy and specificity to validate the clinical efficacy and practical feasibility among high risk pregnancies. The prenatal sample may contain maternal tissue contamination which are eliminated by analyzing multiple single cell PCR analysis. Further, multiple polymorphic markers are employed to ensure its fetal origin in multiplex PCR to analyze prenatal DMD diagnostics. This distinguishes between maternal tissue contamination and CVS cells and confirms the single cell PCR performance for deletions analysis of true CVS cells.

Single-cell multiplex PCR is performed using HotStar-Taq™ DNA Polymerase (Qiagen, Valencia, Calif.) following the guidelines for single-cell PCR given in the HotStar-Taq PCR Handbook (Qiagen). Fluorescent multiplex single cell PCR protocol for different mutations of DMD gene is analyzed. Single cells are analyzed for the presence or absence of the exons 45, 48, 49, 43, 19, 3, 8, 13 and the promoter region of the human dystrophin gene for comparison. The cells loaded in the chip along with lysis buffer and PCR master mix react with the dried primers spots in the chip during the PCR amplification. The cDNA are amplified with fluorescent PCR, and fluorescent signals are detected by the fluorescent scanner.

Example 2: Diagnostics of Cancer

The analysis of heterogeneity in individual tumor cell represents a major step in developing a precise molecular signature of a patient's cancer which leads to therapies tailored to individual patients, an important objective for new oncology drugs. At such single cell level, preamplification of the entire mRNA library to analyze a multigene reverse transcription-PCR panel without compromising the sensitivities of individual marker genes is required. Circulating tumor cells (CTCs) that circulate in the bloodstream alongside normal cells represent a "real-time" biopsy with a surrogate source of tissue in cancer diagnosis and prognosis. The inhomogeneities in the tumor cells and their flow in to blood stream require interrogation of the individual tumor cells and comparison of individual CTCs' expression levels. The ability to quantify and profile the gene expression of CTCs allows improved biological characterization of cancer diagnostics in real time and expedite the development of effective patient-specific therapies. Automated enumeration and characterization of multigenes in circulating tumor cell (CTC) from whole blood have widespread implications in the prognosis and diagnosis of cancer. Furthermore, with the ability to multiplex in a massively parallel fashion, several genes can be screened simultaneously and each panel can also contain desired positive and negative controls. Assays to detect cancer cells in blood have been used clinically to provide prognostic and theranostic information and to test for minimal residual disease. This system has the capacity to process thousand of individual cells; detect circulating tumor cells based on multiplexed PCR results; and analyze the presence or absence of the multiple genes. The presence of circulating tumor cells in the blood can be detected at the single cell level in a population with thousands or more cells by applying single cell PCR assays using expressed mRNA or micro RNA and Philadelphia chromosome positive acute lymphoblastic leukemia (Ph+ ALL) are characterized at the molecular level by the bcr-abl fusion transcript. The early detection of mutations in the Bcr-Abl fusion tyrosine kinase by SC-PCR in a cell population may allow timely treatment intervention to prevent or overcome resistance.

Example 3: Diagnostics Using Clinical Samples

Diagnostics using clinical samples is important for routine and non-invasive testing of patients undergoing therapy. For example, Hepatitis C virus (HCV), is a major cause of chronic liver disease, with an estimated 200 million people affected worldwide. Despite recent success after the introduction of combination therapy with interferon (IFN)-α and ribavirin, resistance to antiviral therapy remains a serious problem in the management of chronic hepatitis C. The absence of HCV in the serum of patients by the end of treatment, does not exclude future viremia. The most extrahepatic site for the virus is peripheral blood mononuclear cells (PBMC) and these cells are considered as a potential reservoir of HCV infection. The patient might still be a source of infection to others and so it is strongly encouraged to test for HCV in PBMC to detect lack of response to treatment and persisting infection. Ultrasensitive and specific non-invasive and risk-free monitoring systems that measure very low levels of HCV in blood have been of greater significance for diagnostics and prognostics. The programmable microarray based single cell diagnostics system performs rapid, sensitive, specific and reproducible quantitative monitoring of HCV RNA in PBMCs. This new technology featured by processing very minute amount of samples and reagents has the potential to detect wide variety of liver diseases simultaneously in the frequency domain by digitally analyzing statistically significant samples. The system is useful not only for the diagnostics but also for therapeutics and discovery of new vaccine which has also been hampered by the great heterogeneity of the HCV genome.

Example 4: Diagnosis of Infectious Diseases

Diagnostics of infectious diseases requires and automatic one touch analysis of blood sample or other cells. Precise molecular analysis on single cells from a large population of cells led to the enumeration of cells with specific genes. For example HIV/AIDS diagnosis can be performed by analysis of single PBMC cells for the presence or absence of cell-associated HIV viral genomic RNA and the mRNA of β-actin. Researchers often purify DNA from blood samples prior to performing PCR because it is believed that blood constituents and the reagents commonly used to preserve blood samples (e.g., anticoagulants) interfere with PCR. But in the case of single cell PCR such purification process is not required and high throughput such PCR reactions can be used for the enumeration of CD4 cells which are specifically targeted and destroyed by HIV. A healthy person's CD4 count can vary from 500 to more than 1,000. Even if a person has no symptoms, HIV infection progresses to AIDS when his or her CD4 count becomes less than 200. Prompt diagnosis and treatment can reduce or delay the onset of some serious complications, such as opportunistic infections, and can improve quality of life. In some cases, rapid treatment with medication can prevent the development of HIV/AIDS after exposure to the HIV virus. Normal PBMC and human immunodeficiency virus (HIV) type-1 infected PBMC cells can be distinguished in RT-PCR. The mRNAs released from the cell are reverse transcribed into cDNA using Sensiscript™ Reverse Transcriptase in the enzyme mix.

Example 5: Applications in Biomedical Research

Single-cell PCR has proven to be of enormous use to basic scientists, addressing diverse immunological, neurological, and developmental questions, where both the genome and also messenger RNA expression patterns are examined. Enhancements in sensitivity with Single cell PCR permits scientists to investigate changes at the level of a single cell, far below what are needed using traditional methods. The understanding of many biological processes would greatly benefit from the ability to analyze the content of single cells.

The advantage of diagnosing a patient's cancer at the single cell level provides us an approach for early detection of cancer and yield insights into how cancer cells are responding or adapting to therapy. An extended single cell technique predicts the pathways of cancer cells that circumvent current therapies and direct the patient towards alternative treatments more intelligently.

The goal in forensic science is to eliminate uncertainty, using technology to precisely determine identity. Researchers continue to refine and improve forensic methods using single cell analysis with success for both increased sensitivity and cost savings.

Fetal cells can be found circulating in maternal blood. Fetal cells recovered from maternal blood provide the only source for noninvasive prenatal DNA diagnosis. Recently, genetic diagnosis using fluorescent PCR has been applied at the single-cell level for sex or single-gene defect diagnosis.

Circulating tumor cell levels in blood may serve as a prognostic marker and for the early assessment of therapeutic response in patients with metastatic cancer, and are an independent prognostic factor at primary diagnosis. The presence of circulating tumor cells in the blood can be detected at the single-cell level, by applying single-cell PCR assays. This technology can be extended to diagnostics of various diseases. Small concentration changes and/or altered modification patterns of disease-relevant components, such as mRNA and/or micro RNA, have the potential to serve as indications of the onset, stage, and response to therapy of several diseases. Current single cell PCR methods use individual cells of interest isolated by micromanipulation or cell sorting. Low abundance mRNA is often lost during cell lysis and extraction process. These methods are extremely labor intensive and require expensive equipment to isolate single cells and perform PCR on each cell. However, to detect rare abnormal cells, a large number of cells must be analyzed spontaneously.

Example 6 Applications in iPS Cells

The system will help to understand the relationship between stochastic variations of gene expression within individual iPS cells and heterogeneous transcriptional profiles across a population of cells. This platform would be very useful for accurately quantifying the differentiation process and to serve as a performance metric of every step of stem cell differentiation process for regenerative medicine. Although only non-tumorigenic differentiated iPSC derivatives are posited for transplantation, it is still difficult to be certain that undifferentiated, tumorigenic cells do not still exist in these differentiated populations. Single cell gene expression, RT-PCR protocol in nanoliter to picoliter volumes for the genes that indicate undifferentiated state (Nanog or Oct-4) and the gene that indicate differentiated states (Pax6 or Sox1) is very useful. The signal for β-actin mRNA will be the indicator whether the RT-PCR system works successfully with each individual cell. The cells will be premixed with lysis buffer, primers and RT-PCR master mix and will be flowed through the cell inlet on the chip for single cell trapping, encapsulation and RT-PCR. The RT-PCR will be performed in a single fluidic step and the fluorescent signals of the amplified cDNA will be detected by continuous fluorescent imaging during the thermal cycling.

Example 7 Applications in Combinatorial Drug Screening

Combinatorial drug screening for cell based drug discovery and efficacy is increasingly dependent on high-throughput technologies due to the need for more efficient screening of multiple combinatorial drug candidates. Miniaturized reactors have been developed to reduce culture volume, increase process efficiency and to administer chemotherapeutic drugs sequentially or together in combination. The use of combination therapies can lead to increased efficacies at significantly lower doses and side-effects and so investigation of combination therapies for curative and palliative care is very significant. A fully automatic Programmable Array of Living cells (PAL) can integrate on-chip generation of drug concentrations and pair-wise combinations with parallel culture of cells for drug candidate screening applications. This example can be applied to cancer drug screening by performing cell based bioassay for understanding disease pathways in drug discovery or optimization. The device can be initially applied to chemotherapeutic drugs as sensitizer for TRAIL-induced cell death and extended to identifying combinatorial drug treatments for a variety of diseases. The ability to carry out sequential and simultaneous treatments also facilitates exploration of diverse dosing studies in toxicology and biology.

1. It is to be appreciated that the invention has been described hereabove with references to certain examples or embodiments of the invention but that various additions, deletions, alterations and modifications may be made to those examples and embodiments without departing from the intended spirit and scope of the invention. For example any element or attribute of one embodiment or example may be incorporated in to or used with another embodiment of example unsuitable for intended use. All reasonable additions, deletions, modification and alterations are to be considered equivalents of the described examples and embodiments and are to be included within the scope of the following claims.

The invention claimed is:

1. A microfluidic device for performing cell analysis, the microfluidic device comprising:
   a microfluidic chip having a plurality of encapsulated reactors, at least one of the plurality of encapsulated reactors comprising:
   a plurality of micropillars configured to form a trapping site for trapping a single non-encapsulated cell;
   an immiscible fluid encapsulating the plurality of micropillars and the single cell.

2. The microfluidic device of claim 1, wherein the at least one of the plurality of encapsulated reactors is a picoliter reactor.

3. The microfluidic device of claim 1, wherein the immiscible fluid comprises vegetable oil, mineral oil, fluorocarbonated oil, oil with different composition of surfactants, paraffins, or aqueous fluids configured to undergo a physical transition.

4. The microfluidic device of claim 1, further comprising a hot reservoir containing a hot immiscible fluid and a cold reservoir containing a cold immiscible fluid for performing thermal cycling.

5. The microfluidic device of claim 4, wherein the hot reservoir and the cold reservoir are isolated.

6. The microfluidic device of claim 4, further comprising a pump and a set of valves for circulating the hot immiscible fluid and the cold immiscible fluid.

7. The microfluidic device of claim 1, wherein the plurality of micropillars include an inner layer of micropillars configured to trap the single cell, and an outer layer of micropillars configured to prevent the immiscible fluid from contacting with the single cell.

8. The microfluidic device of claim 7, wherein a space between the inner layer of micropillars and the outer layer of micropillars is configured to maintain reagents around the single cell.

9. The microfluidic device of claim 8, wherein the reagents include drugs, cell media or nutrition.

10. The microfluidic device of claim 7, wherein the inner layer of micropillars and the outer layer of micropillars are concentric.

11. The microfluidic device of claim 1, wherein the at least one of the plurality of encapsulated reactors further includes guiding pillars configured to funnel the single cell into the trapping site.

12. The microfluidic device of claim 1, wherein the plurality of micropillars are configured to facilitate a formation of an isolated droplet around the trapping site.

13. The microfluidic device of claim 1, wherein the microfluidic chip is configured to perform in-situ sample processing of molecules or genes from the single cell using electro-magnetic fluidic.

14. The microfluidic device of claim 1, further comprising a slip and lock chip for performing multistep chemical reaction.

15. The microfluidic device of claim 1, wherein the plurality of micropillars include at least three micropillars for trapping the single cell, and additional micropillars below the at least three micropillars to increase a volume of a trapped aqueous fluid in the at least one of the plurality of encapsulated reactors.

16. The microfluidic device of claim 1, wherein the at least one of the plurality of encapsulated reactors is configured to perform single cell polymerase chain reaction (PCR).

* * * * *